(12) United States Patent
Aguilera et al.

(10) Patent No.: US 6,605,254 B2
(45) Date of Patent: Aug. 12, 2003

(54) METHOD USING ETHYLENE OXIDE TO FUMIGATE CORROSION PROMOTING MICROBES

(75) Inventors: Anthony Mark Aguilera, Glendale, AZ (US); Ronald Gordon Bitney, Kligma, AZ (US); Stephen Alan Conviser, Morristown, NJ (US); Barbara Ruth Decaire, Amherts, NY (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/756,488

(22) Filed: Jan. 8, 2001

(65) Prior Publication Data

US 2002/0006354 A1 Jan. 17, 2002

Related U.S. Application Data

(60) Provisional application No. 60/175,204, filed on Jan. 10, 2000.

(51) Int. Cl.[7] .............................. A61L 9/00; F02D 7/00; F26B 5/04; A62C 35/00; B08B 5/00
(52) U.S. Cl. ................................ 422/28; 422/1; 422/6; 422/12; 422/32; 422/40; 422/123; 122/379; 34/403; 34/404; 34/410; 34/437; 169/5; 169/11; 239/104; 239/105; 239/106; 239/108; 239/112; 134/11; 134/22.11; 134/26; 134/34; 134/37; 134/42; 510/247
(58) Field of Search .......................... 422/1, 6, 12, 14, 422/16–17, 26–30, 32–37, 40–41, 120, 123, 125; 122/379; 34/403–404, 410, 437; 169/5, 11; 239/104–105, 106, 108, 112; 134/11, 21.11, 22.11, 22.12, 22.13, 22.14, 22.17, 22.19, 26, 29, 30–31, 34, 36–37, 42; 510/108–109, 195, 247, 412

(56) References Cited

U.S. PATENT DOCUMENTS

| 4,681,739 A | | 7/1987 | Rosenblatt et al. ............ 422/37 |
|---|---|---|---|
| 5,039,485 A | | 8/1991 | Conviser et al. ............... 422/34 |
| 5,160,047 A | | 11/1992 | McCarthy .................... 210/749 |
| 5,254,309 A | | 10/1993 | Felix et al. .................... 422/34 |
| 5,342,579 A | | 8/1994 | Conviser et al. ............ 514/475 |
| 5,376,333 A | | 12/1994 | Shankland et al. ........... 422/34 |
| 5,749,203 A | * | 5/1998 | McGowan, Jr. |
| 5,885,364 A | | 3/1999 | Hieatt et al. ............. 134/22.11 |
| 5,976,554 A | * | 11/1999 | Richard et al. |
| 6,076,536 A | * | 6/2000 | Ludwig et al. |

FOREIGN PATENT DOCUMENTS

| WO | WO 99/42143 | | 8/1999 | |
|---|---|---|---|---|
| WO | WO 99/42144 | * | 8/1999 | ............. A61L/2/20 |

* cited by examiner

Primary Examiner—Robert J. Warden, Sr.
Assistant Examiner—Monzer R. Chorbaji
(74) Attorney, Agent, or Firm—Deborah M. Chess; Colleen D. Szuch

(57) ABSTRACT

The present invention relates to a method of fumigating closed systems susceptible to microbially influenced corrosion (MIC). The method is particularly useful in a method for mitigating MIC in fire protection sprinkler systems.

22 Claims, No Drawings

METHOD USING ETHYLENE OXIDE TO FUMIGATE CORROSION PROMOTING MICROBES

This application claims the benefit of provisional application Ser. No. 60/175,204, filed Jan. 10, 2000.

FIELD OF THE INVENTION

The present invention relates to the fumigation and maintenance of closed systems that are susceptible to microbially influenced corrosion (MIC).

BACKGROUND

The maintenance of systems that corrode over time due to microorganism contamination is a significant challenge due to the proliferation, resilience and adaptability of microorganisms. A large number and variety of systems are susceptible to such degradation, and while a variety of methods have been devised to address these systems, including cleaning and scraping, the need exists for a method that addresses the root causes of the corrosion, and that is capable of safe and effective use in a wide variety of systems, irrespective of the material composition of the system.

Systems manufactured of metals, and metal alloys, are particularly susceptible to damage from microbes. These effects are seen predominately in piping and other enclosed systems, where microbially influenced corrosion and biofouling cause occlusion, leaks, and premature failure of materials of construction. There are several types of bacteria responsible for the deterioration, often with more than one species observed in a pipe sample. These bacteria can be found both in installed systems, and on pipe that has never been in service. Without treatment, these microbes multiply, damaging the system and contaminating its contents. While metal systems are particularly susceptible to corrosion, plastic constructions are also susceptible to microbial degradation, which is enhanced by combinations of factors, including environmental factors, such as temperature and solar radiation. These factors combine with the processes promoted by contaminating microorganisms to foul systems, and lead to system failure.

Microbial damage affects a vast number of enclosed systems, ranging from tanks and vessels to piping systems. Potential applications of this anti-microbial treatment include fire protection sprinkler systems, water purification and delivery equipment, cooling towers, ballast systems, and manufacturing or chemical processing, handling and storage equipment.

Commercially available system maintenance treatment options include flushing systems with liquid disinfectants and cleaning solutions such as glutaraldehyde (U.S. Pat. No. 5,160,047) or glycolic acid solution (U.S. Pat. No. 5,885,364). Liquid disinfectants are limited in their ability to reach every surface in the system since it is difficult to flush thoroughly every branch and upright section of an extensive network of piping. Any bacteria that are not directly exposed to the disinfectant will reproduce.

Gaseous sterilizing agents such as ethylene oxide and chlorine dioxide are known and have been used for fifty years in the medical industry to sterilize medical instruments and equipment. Both chlorine dioxide and pure ethylene oxide are explosive. However, nonflammable sterilant blends with an inert carrier gas are commercially available.

The potential effectiveness of fumigants in a method to fumigate systems that are susceptible to microbially influenced corrosion (MIC) is not known. In particular, ethylene oxide is known to be more effective on porous materials than non-porous. Applicants have discovered that, when used in the methods of the present invention, fumigants, and in particular ethylene oxide, may be effectively employed to uniformly expose the inner surface of a system and penetrate layers of corrosion products and/or microorganism growth present on the system inner surfaces to reach the underlying microorganisms of the type that influence corrosion. The method has a wide range of applications but is particularly useful for mitigating MIC in fire protection sprinkler systems.

SUMMARY OF THE INVENTION

The present invention relates to a method of fumigating a closed system containing articles or means in which aqueous media is contained or through which aqueous media flows, which method comprises exposing the surfaces of the article or means or to an effective amount of a fumigant for an effective time of exposure.

More particularly, the invention relates to a method of fumigating a closed system containing articles or means in which aqueous media is contained or through which aqueous media flows, which method comprises evacuating the system; introducing an effective amount of a fumigant; exposing the system to the fumigant for an effective time of exposure; and removing the fumigant.

In a preferred embodiment of the method of the invention, the fumigant comprises a non-flammable blend of ethylene oxide and an inert carrier gas.

In another preferred embodiment, the method comprises humidifying the system to about 30–90% relative humidity, preferably about 50 to about 80% relative humidity prior to introducing the fumigant.

In still another preferred embodiment, the method comprises adding heat to the system to accelerate the biocidal activity of the fumigant.

In yet another preferred embodiment, the method comprises exposing the system to the fumigant under subatmospheric pressure, preferably between about 0.5 and less than 1 atm.

DETAILED DESCRIPTION OF THE INVENTION

The systems treated by the present method comprise articles or means having outer and inner boundaries wherein the inner boundary defines a space. This space is bounded by the inner surfaces of the article, which space may extend directionally and define passageways through which fluids may flow. Said inner surfaces may be of any configuration such as curvaceous or flat and illustratively but not limited to forming a cylindrical or tubular space, or a polygonal space such as triangular or rectilinear space. The articles enclosing these spaces are typically designed to comprise one or more openings providing for the introduction and elimination of said fluids. Exemplary systems include enclosed articles (closed systems) such as tanks, vessels, piping, conduits, couplings, valves, and tubing of all shapes and sizes.

The systems are constructed of a variety of materials by any known process including extrusion, molding, casting, milling, annealing, thermoforming, cutting, drilling, bending, etc. Material properties related to the use of the articles are generally characterized by mechanical strength, chemical resistance, durability, and resistance to heat, light, oxygen, and moisture. In particular the materials comprising the articles are typically chemically resistant to the fluid(s) that contact the inner surfaces of the article, including the fumigants disclosed herein to treat the surfaces at the conditions of exposure. Exemplary materials include metals and plastics. Illustrative metals are copper, iron, steel, aluminum, and alloys thereof and coated metals such as zinc coated steel. Illustrative plastics include elastomers, polyvinyl chloride (PVC), chlorinated PVC, polybutylene, nylon, polyurethane, polyolefin, polycarbonate any of which may incorporate additives including fillers, pigments, plasticizers, antioxidants, flame retardants and UV light stabilizers.

Microbially influenced corrosion (MIC) refers to degradation or corrosion as a result of coming into contact with, or providing suitable growth conditions for, microorganisms that promote and/or catalyze material corrosion processes. The types of bacteria known to cause MIC are low nutrient bacteria (LNB), iron related bacteria (IRB), sulfate reducing bacteria (SRB) and acid producing bacteria (APB). They may also be referred to as metal-damaging microbes.

As used herein the term "fumigate" means to subject to fumes in order to destroy, neutralize or inhibit the growth of microorganisms that influence corrosion. Fumigation of that results in a reduction of at least two logs, and preferably three or more logs, of the contaminating microorganisms is desirable.

The term "fumigant" means an agent in vapor form that is toxic to microbes that influence corrosion. Suitable fumigants include alkylene oxides, chlorine dioxide, fluorine dioxide, ozone, hydrogen peroxide, methyl bromide and the like for an amount of time sufficient to fumigate said systems. Preferred alkylene oxides are ethylene oxide and propylene oxide. Ethylene oxide is particularly preferred.

By itself, ethylene oxide is an extremely flammable gas. Thus, when ethylene oxide is used alone as a fumigant, precautions such as explosion proof equipment are mandatory. A preferable practice is to blend the ethylene oxide with an inert carrier gas that serves to dilute the ethylene oxide and render the mixture as a whole non-flammable. See U.S. Pat. Nos. 5,039,485; 5,254,309; 5,342,579; 5,376,333; 5,976,554; and WO 99/42143, all of which are incorporated by reference herein in their entirety. Exemplary inert carrier gases include but are not limited to carbon dioxide, nitrogen, halogenated hydrocarbons and mixtures thereof Exemplary halogenated hydrocarbons include chlorofluorocarbons, hydrochlorofluorocarbons and hydrofluorocarbons that are gases at or below atmospheric pressure and at temperatures of about 0° C. and above. Examples of suitable commercially available halogenated hydrocarbon compounds include, but are not limited to, chlorofluorocarbons such as dichlorodifluoromethane (CFC-12); hydrochlorofluorocarbons such as chlorodifluoromethane (HCFC-22) and 1-chloro-1,2,2,2-tetrafluoroethane (HCFC-124); hydrofluorocarbons such as pentafluoroethane (HFC-125), 1,1,1,2-tetrafluoroethane (HFC-134a), 1,1,1,3,3,3-hexafluoropropane (HFC-236fa), 1,1,1,2,3,3,3-heptafluoropropane (HFC-227ea) and 1,1,1,2,2,3,3-heptafluoropropane (HFC-227ca); and combinations any of the above. Hydrofluorocarbons are particularly preferred due to their low ozone depletion potentials. Particularly preferred hydrofluorocarbons are pentafluoroethane, heptafluoropropane and mixtures thereof. A particularly preferred fumigant comprises about 8 to about 25 weight % ethylene oxide, about 75 to about 92 weight % pentafluoroethane, and about 5 to about 15 weight % heptafluoropropane.

An effective amount of fumigant is an amount that is effective to destroy, neutralize or inhibit the growth of harmful microorganisms present in the system under treatment. For example, an effective amount of ethylene oxide typically ranges from a concentration of about 200 mg/l to about 1250 mg/l, preferably 300 mg/l to about 700 mg/l. In a particular system, the preferred effective amount may be determined by routine experimentation. The concentration of ethylene oxide is set by the pressure of the gas in the system and can be calculated using Raoult's law. For example, when the pressure of the system is 745 mmHg, the concentration of ethylene oxide is about 350 mg/l.

The sealed system is evacuated by means of a suitable vacuum pump. The size of the vacuum pump is readily selected by one skilled in the art, and is determined by the volume of the system to be evacuated, the desired ultimate level of vacuum, and the time required to reach the desired vacuum level. The desired level of vacuum varies with each specific application. In general, high levels of vacuum are preferred. Vacuum levels of less than or equal to about 10 mm Hg are especially preferred.

The fumigant supply cylinder is connected to the system to be treated using appropriate piping fittings. All piping, valves, fittings between the main cylinder valve and the system are open to the system during the evacuation step described above. When the desired vacuum level is reached, the system is isolated from the vacuum source. Gas is admitted to the system by opening the main cylinder valve. It may be desirable to have a heat exchanger or vaporizer at the cylinder outlet to assist in evaporating liquefied compressed gases, such as ethylene oxide or blends of ethylene oxide with fluorocarbon diluents. The concentration of ethylene oxide in the system is related to the system pressure, and may be calculated using Raoult's law by one skilled in the art. For example, a pressure rise of about 745 mm Hg above the final vacuum level introduces about 350 mg ethylene oxide per liter of fumigated volume. When the desired system pressure is reached, the valve on the fumigant supply cylinder is closed.

The effective time of exposure is that time sufficient to fumigate the inner surfaces of the articles making up the system. An effective amount of exposure for a contaminated article is typically from about one hour to about five days, although longer exposure times may be employed if desired. The optimum exposure time for a particular system may be determined by routine experimentation.

Since a moist organism is more susceptible to the action of the fumigant, water vapor is typically employed. The present method may provide for the presence of water vapor by a variety of means, including providing an atmosphere of controlled humidity either concurrently with or prior to introduction of fumigant to the system. In one embodiment, the method comprises the pretreatment of the system by evacuating the system until the relative humidity therein reaches a level of about 30 to about 90%, most preferably between about 50 to about 80% and then exposing the inner surfaces of the system or article to an effective amount of fumigant.

In a preferred embodiment of the humidification procedure of this invention, the system is humidified to a relative humidity above about 60%, e.g., about 70 to about 95%, for at least about 15 minutes, and preferably for about 20 minutes to about one or more hours, immediately prior to introducing the fumigant. Humidification may be accomplished in several ways. Water vapor may be introduced via steam injection or water vapor may be obtained by evaporating water from a cylinder containing degassed water. The humidity level may be monitored by system pressure gauge, or using commercially available humidity meters. Other means of introducing water vapor to the system will be obvious to those skilled in the art. Humidification may be conducted at about room temperature, although lower or higher temperatures may be employed if desired. It should be noted that other humid gases such as humidified nitrogen, etc. may be employed.

The addition of heat to the system enhances fumigation efficiency (lower concentration of gas or shorter exposure time). In general, a 10° C. increase in temperature doubles the rate of fumigation. In a particular embodiment of the invention, steam may be used to both humidify and add heat to the system.

The practice of the present method requires attention to matters of safety, including the safe handling of the gaseous materials used in the present invention, as well as the formulation of the gaseous material itself In this connection, the present method introduces the fumigant into the enclosed space of the system and the space is closed for an effective time of exposure. Due to safety considerations, it is preferred to use a pressure within the closed system at or below atmospheric pressure so as to limit leakage of the gas into the environment. Consequently, it is most preferred to expose the inner surfaces of the system to a gas at pressure of between about 0.5 and less than 1 atm pressure.

Another safety aspect of the present invention comprises the steps taken after the biocidal action of the fumigant has been achieved. At such time, the fumigant is removed from the system and recovered in an appropriate recovery apparatus or destroyed. Such a method may involve the repeated flushing of the system with an inert gas, such as nitrogen gas, and the pressurization of the exhausted fumigant into a tank suitable for proper disposal, or recycling. Ethylene oxide is highly reactive and is susceptible to reaction or catalytic destruction as a means of disposal. For example, passing the exiting gas stream through a scrubber system containing either an acidic or basic solution will convert the ethylene oxide to ethylene glycol and polyethylene glycols. Alternatively, flowing the ethylene oxide-containing stream through a catalytic bed containing Hopcalite, or other commercially available catalyst, is an effective means of destruction.

Additional steps may be taken to prevent recontamination of the fumigated system. Such steps may include the sealing of all system openings or portals that may permit the reintroduction of contaminating bacteria. Suitable seals, covers and closures that provide effective barriers to the passage of microorganisms may comprise of a variety of materials depending on the nature of the systems being treated, for example, nonporous materials such as metals, plastics, glass and ceramics. Porous materials may also perform acceptably provided that the pore size of the material is sufficiently small to prevent the passage of microorganisms.

Furthermore, systems that hold water during normal operation may be filled with sterile water prepared by any known sterilizing method, including ozonolysis, distillation or microfiltration. Recontamination of the system by waterborne microorganisms is avoided by the use of sterile as opposed to municipal water. An additional advantage to filling ethylene-oxide-sterilized systems with sterilized water is the promotion of the hydrolytic conversion of residual ethylene oxide. Systems that typically hold water over extended periods of time include fire protection sprinkler systems. Fire protection sprinkler systems are a preferred embodiment of the invention.

Although not essential to the practice of the present method, in some applications, it may be advisable to monitor the residual levels of viable microorganisms in system to allow early detection of recontamination.

The present inventive method in a specific aspect is practiced by sealing the system to be treated and evacuating the system, while retaining or establishing a relative humidity of 30–80% in the system. This may be accomplished by adding water vapor to a relatively dry system, or by evacuating the water from a wet system until the desired level of water vapor remains. A fumigant comprising a nonflammable ethylene oxide mixture is admitted to the system until the desired effective concentration of ethylene oxide gas is reached. In one preferred embodiment of the invention, the system pressure remains just below ambient atmospheric pressure. This pressure limitation ensures that in the event of a system leak, room air will enter the system rather than toxic ethylene oxide leaking out into the surrounding environment. The ethylene oxide blend is then allowed to remain in the system for a period of time sufficient to penetrate and kill microbes that influence corrosion present therein. After exposure, the ethylene oxide blend is removed from the system and may be recovered using refrigerant recovery equipment consisting of a vacuum pump, compressor, and receiver cylinder.

The following non-limiting example illustrates the practice of the invention.

EXAMPLE

Nine pipe samples, each three feet in length, from fire protection sprinkler system equipment contaminated with corrosion-causing microbes are used in this example. Each sample is equipped with a sprinkler head installed at midlength. Three of the samples are of pipe that has never been in service; the remaining six are of pipe that has been removed from service. Of these six sections, three are treated with an acid cleaning solution that removes visible corrosion products, including rust, tubercles, and biofilm. The nine samples are then cultured to test for the presence of four types of bacteria known to cause microbially influenced corrosion (MIC). These bacteria are referred to as low nutrient bacteria (LNB), iron related bacteria (IRB), sulfate reducing bacteria (SRB) and acid producing bacteria (APB). Initially, all four bacteria types are present on the samples.

The pipes are drained of residual water, dried with compressed nitrogen gas, and evacuated until the relative humidity reaches a level of 75%. One pipe from each source is isolated from the rest of the treatment procedure to serve as a control pipe sample. Next, a fumigant mixture comprising 10.4 weight percent ethylene oxide, 81.9 weight percent pentafluoroethane (HFC-125), and 7.7 weight percent heptafluoropropane (HFC-227ea) is introduced into the six test pipes until the system pressure is just below ambient atmosphere pressure, about 745 mm Hg. At this pressure, the concentration of ethylene oxide in the system is 350 mg/l. The gas remains in three of the test pipes for about one day. The other test samples are exposed for a period of three days. At the end of the exposure period, the system is alternately flushed with dry compressed nitrogen gas and evacuated using a vacuum pump until such time that a portable ethylene oxide monitor does not detect any ethylene oxide in the exhaust gas. The pipe samples are then re-analyzed for the presence of bacteria.

Table 1 shows that exposure to the fumigant significantly reduces the number of microorganisms present as compared to untreated pipe samples.

TABLE 1

Comparison of Bacteria Levels in Untreated Pipe vs. Pipe Exposed to Fumigant

| Sample | Gas Exposure | LNB (organisms/ml) Pre | LNB (organisms/ml) Post | IRB (organisms/ml) Pre | IRB (organisms/ml) Post | SRB (organisms/ml) Pre | SRB (organisms/ml) Post | APB (organisms/ml) Pre | APB (organisms/ml) Post |
|---|---|---|---|---|---|---|---|---|---|
| Installed pipe | None | 20 | 190 | <3 | <3 | 4600 | <3 | <3 | 180 |
|  | 1 Day | <10 | <10 | <3 | <3 | ≧11000 | <3 | <3 | <3 |
|  | 3 Days | <10 | <10 | <3 | <3 | ≧1100 | <3 | <3 | <3 |
| Installed pipe | None | <10 | <10 | <3 | <3 | <3 | <3 | <3 | <3 |
| (acid cleaned | 1 Day | <10 | <10 | <3 | <3 | <3 | <3 | <3 | <15 |
| before test) | 3 Days | <10 | <10 | <3 | <3 | <3 | <3 | <3 | <3 |
| New pipe | None | 61000 | 920000 | <3 | <3 | <3 | <3 | <3 | ≧1100 |
|  | 1 Day | N/T | <10 | N/T | <3 | N/T | <3 | N/T | <3 |
|  | 3 Days | 2700 | <10 | <3 | <3 | <3 | <3 | <3 | 15 |

LNB = Low Nutrient Bacteria
IRB = Iron Related Bacteria
SRB = Sulfate Reducing Bacteria
APB = Acid Producing Bacteria
N/T = not tested

We claim:

1. A method of fumigating a closed system susceptible to microbially influenced corrosion, said closed system comprising an inner surface and one or more openings providing for the introduction and elimination of fluids into said closed system, said method comprising evacuating said system under subatmospheric pressure and introducing an effective amount of a fumigant into said system through at least one of said one or more openings to expose only said inner surface to said fumigant for an effective time of exposure.

2. The method of claim 1 wherein the pressure in the system is between about 0.5 and 1 atm for said evacuating step.

3. The method of claim 2 wherein the pressure in the system is between about 0.5 and 1 atm for said introducing step.

4. The method of claim 2 wherein the fumigant comprises a compound selected from the group consisting of alkylene oxide, chlorine dioxide, fluorine dioxide, ozone, hydrogen peroxide, and methyl bromide.

5. The method of claim 4 wherein the fumigant comprises ethylene oxide.

6. The method of claim 5 wherein the fumigant comprises ethylene oxide and an inert carrier gas.

7. The method of claim 6 wherein the inert carrier gas is a halogenated hydrocarbon.

8. The method of claim 7 wherein the halogenated hydrocarbon is selected from the group consisting of CFC-12; HCFC-22; HCFC-124; HFC-125; HFC-134a; HFC-236fa; HFC-227ea; and combinations of two or more thereof.

9. The method of claim 8 wherein the halogenated hydrocarbon is selected from the group consisting of HFC-125; HFC-227ea; and combinations thereof.

10. The method of claim 9 wherein the fumigant comprises about 8 to about 25 weight % ethylene oxide; about 75 to about 92 weight % HFC-125; and about 5 to about 15 weight % HFC-227ea.

11. The method of claim 10 wherein said closed system further comprises at least one passageway through which fluids may flow.

12. The method of claim 11 wherein said one or more openings provide for the introduction and elimination of fluids in said at least one passageway.

13. The method of claim 12 wherein said system is a water handling system.

14. The method of claim 12 wherein said system is a system through which an aqueous fluid flows.

15. The method of claim 12 wherein said system comprises at least one of a tank, vessel, piping, conduit, coupling, valve, and combinations of two or more thereof.

16. The method of claim 15 wherein the pressure in the system is between about 0.5 and 1 atm for said evacuating step.

17. The method of claim 16 wherein the halogenated hydrocarbon is selected from the group consisting of HFC-125; HFC-227ea; and combinations thereof.

18. The method of claim 15 wherein the fumigant comprises ethylene oxide and an inert carrier gas.

19. The method of claim 18 wherein the fumigant comprises about 8 to about 25 weight % ethylene oxide; about 75 to about 92 weight % HFC-125; and about 5 to about 15 weight % HFC-227ea.

20. The method of claim 12 wherein said system is selected from the group consisting of water purification equipment, water storage equipment, cooling towers, fluid handling systems, and ballast systems.

21. A method of fumigating a closed fire protection sprinkler system, said system comprising at least one inner surface and one or more openings providing for the introduction and elimination of fluids into said system, said method comprising evacuating said system under subatmospheric pressure and introducing an effective amount of a fumigant into said system through at least one of said one or more openings to expose said at least one surface to said fumigant for an effective time of exposure.

22. The method of claim 21 wherein the inert carrier gas is a halogenated hydrocarbon.

* * * * *